(12) United States Patent
Peakman

(10) Patent No.: US 7,049,292 B2
(45) Date of Patent: May 23, 2006

(54) THERAPEUTICALLY EFFECTIVE PEPTIDES RELATED TO PREPROINSULIN

(75) Inventor: Mark Peakman, London (GB)

(73) Assignee: King's College London, London (GB)

( * ) Notice: Subject to any disclaimer, the term of this patent is extended or adjusted under 35 U.S.C. 154(b) by 0 days.

(21) Appl. No.: 10/783,095

(22) Filed: Feb. 23, 2004

(65) Prior Publication Data

US 2005/0176637 A1 Aug. 11, 2005

(30) Foreign Application Priority Data

Jan. 30, 2004 (GB) ................ 0402129.1

(51) Int. Cl.
*A61K 38/10* (2006.01)
*A61K 38/16* (2006.01)
*A61K 38/28* (2006.01)
*A61K 38/04* (2006.01)
*C07K 7/00* (2006.01)

(52) U.S. Cl. ............ 514/12; 514/13; 514/14; 530/303; 530/324; 530/326

(58) Field of Classification Search ........... 530/324, 530/303, 326; 424/93.21; 429/223; 435/243; 514/12–14
See application file for complete search history.

(56) References Cited

U.S. PATENT DOCUMENTS

2002/0058614 A1* 5/2002 Filvaroff et al. ........ 514/3

FOREIGN PATENT DOCUMENTS

WO WO 9634882 A1 * 11/1996

OTHER PUBLICATIONS

Peakman, M., Stevens, E.J., et al. 1999. Naturally Processed and Presented Epitopes of the Islet Cell Autoantigen 1A-2 eluted from HLA-DR4. J. Clin. Invest. 104(10):1449-1457.*
Meierhoff, G., Ott, P.A., et al. 2002. Cytokine detection by ELISPOT: relevance for immunological studies in type 1 diabetes. Diabetes Metab. Res. Rev. 18: 367-380.*
Herold, K. C.; "Achieving Antigen-Specific Immune Regulation"; *The Journal of Clinical Investigation*; vol. 113, No. 3; pp. 346-349 (2004).
Schloot, N.C., et al; "Comparison of Cytokine ELISpot Assay Formats for the Detection of Islet Antigen Autoreactive T Cells Report of the Third Immunology of Diabetes Society T-Cell Workshop"; *Journal of Autoimmunity*; vol. 21; pp. 365-376 (2003).

(Continued)

*Primary Examiner*—Karen Cochrane Carlson
*Assistant Examiner*—Marsha Tsay
(74) *Attorney, Agent, or Firm*—Nixon & Vanderhye

(57) ABSTRACT

A peptide having a sequence comprising or consisting of QPLALEGSLQK.

25 Claims, 4 Drawing Sheets

OTHER PUBLICATIONS

Arif, S., et al; "Autoreactive T Cell Responses Show Proinflammatory Polarization in Diabetes but a Regulatory Phenotype in Health"; *The Journal of Clinical Investigation*; vol. 113, No. 3; pp. 451-463 (2004).

Congia, M., et al; "T Cell Epitopes of Insulin Defined in HLA-DR4 Transgenic Mice are Derived from Preproinsulin and Proinsulin"; *Proc. Natl. Acad. Sci.*; vol. 95; pp. 3833-3838 (1998).

Durinovic-Bello, I., et al; "Predominantly Recognized ProInsulin T Helper Cell Epitopes in Individuals With and Without Islet Cell Autoimmunity"; *Journal of Autoimmunity*; vol. 18, pp. 55-66; (2002).

Astill, Tom; "Characterisation of T Cell Epitopes of Proinsulin in Type 1 Diabetes"; Selected Portion of a PhD Thesis; Figures refer to the sequence claimed—the thesis text is as for the Arif et al (2004) publication.

Congia, M., et al; "T cell epitopes of insulin defined in HLA-DR4 transgenic mice are derived from preproinsulin and proinsulin"; *Proc. Natl. Acad. Sci. USA*; vol. 95, No. 7; pp. 3833-3838, Mar. 31, 1998; XP-002204284.

Geluk, A., et al; "HLA-DR Binding Analysis of Peptides from Islet Antigens in IDDM"; *Diabetes*; vol. 47, No. 10; pp. 1594-1601, Oct. 1998; XP-002323217.

Narendran, P., et al; "Humoral and cellular immune responses to proinsulin in adults with newly diagnosed type 1 diabetes"; *Diabetes/Metabolism Research and Reviews*; vol. 19, No. 1; pp. 52-59; Oct. 28, 2003; XP-002323390.

Liberman, S.M., et al; "A comprehensive guide to antibody and T-cell responses in type 1 diabetes"; *Tissue Antigens*; vol. 62, No. 5; pp. 359-377; Nov. 2003; XP-002323391.

Meierhoff, G., et al; "Cytokine detection by ELISPOT: relevance for immunological studies in type 1 diabetes"; *Diabetes/Metabolism Research and Reviews*; vol. 18, No. 5, pp. 367-380; Oct. 2002; XP-002323218.

Peakman, M., et al; "Naturally processed and presented epitopes o the islet cell autoantigen IA-2 eluted from HLA-DR4"; *The Journal of Clinical Investigation*; vol. 104, No. 10; pp. 1449-1457; Nov. 1999; XP-002323392.

Durinovic-BEIIo, I., et al; "Predominantly Recognized Proinsulin T Helper Cell Epitopes in Individuals With and Without Islet Cell Autoimmunity"; *Journal of Autoimmunity*; Vo. 18; pp. 55-56; (2002).

\* cited by examiner

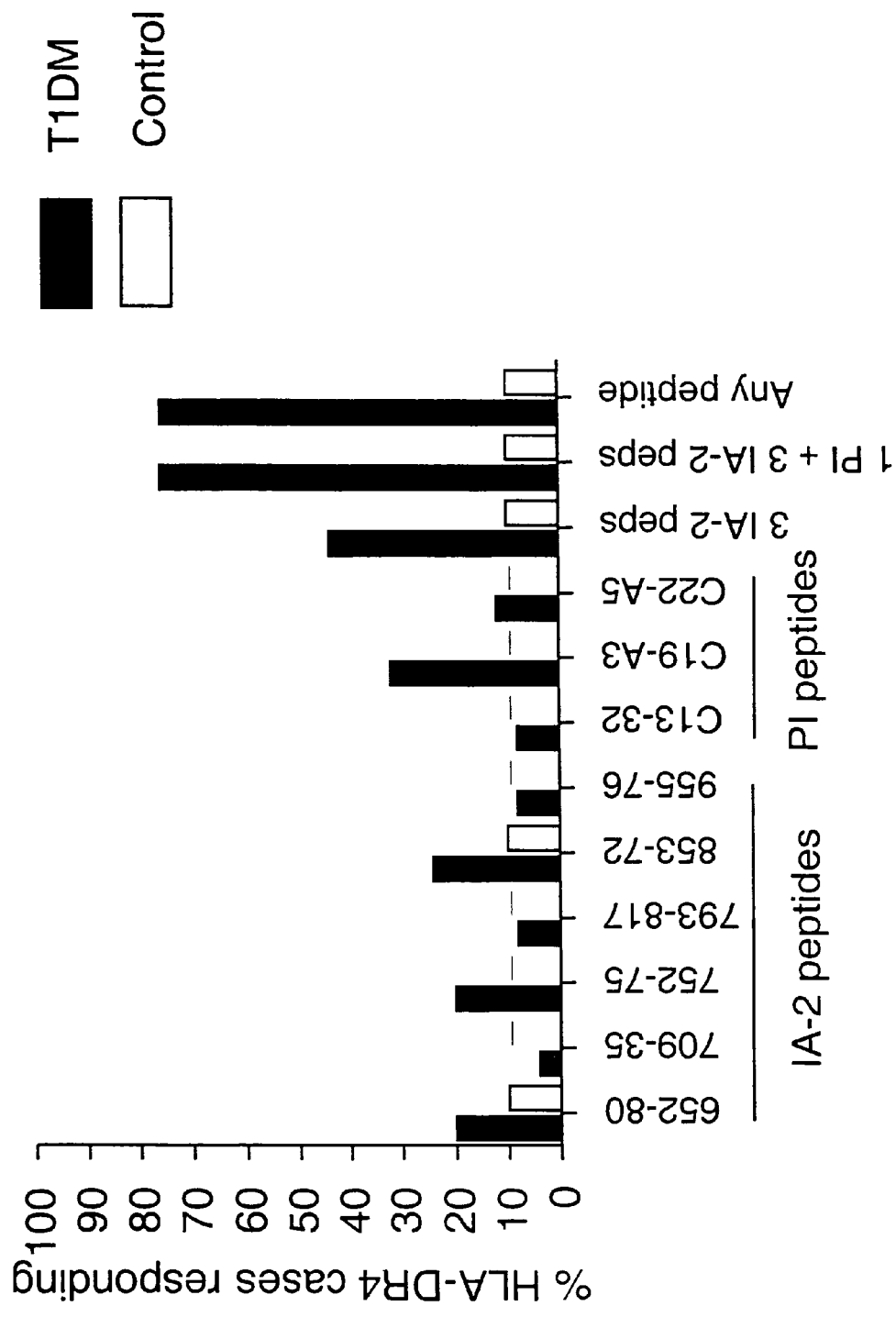
Figure 1. Use of peptides and IFN-γ ELISPOT to identify pathogenic CD4 T lymphocytes

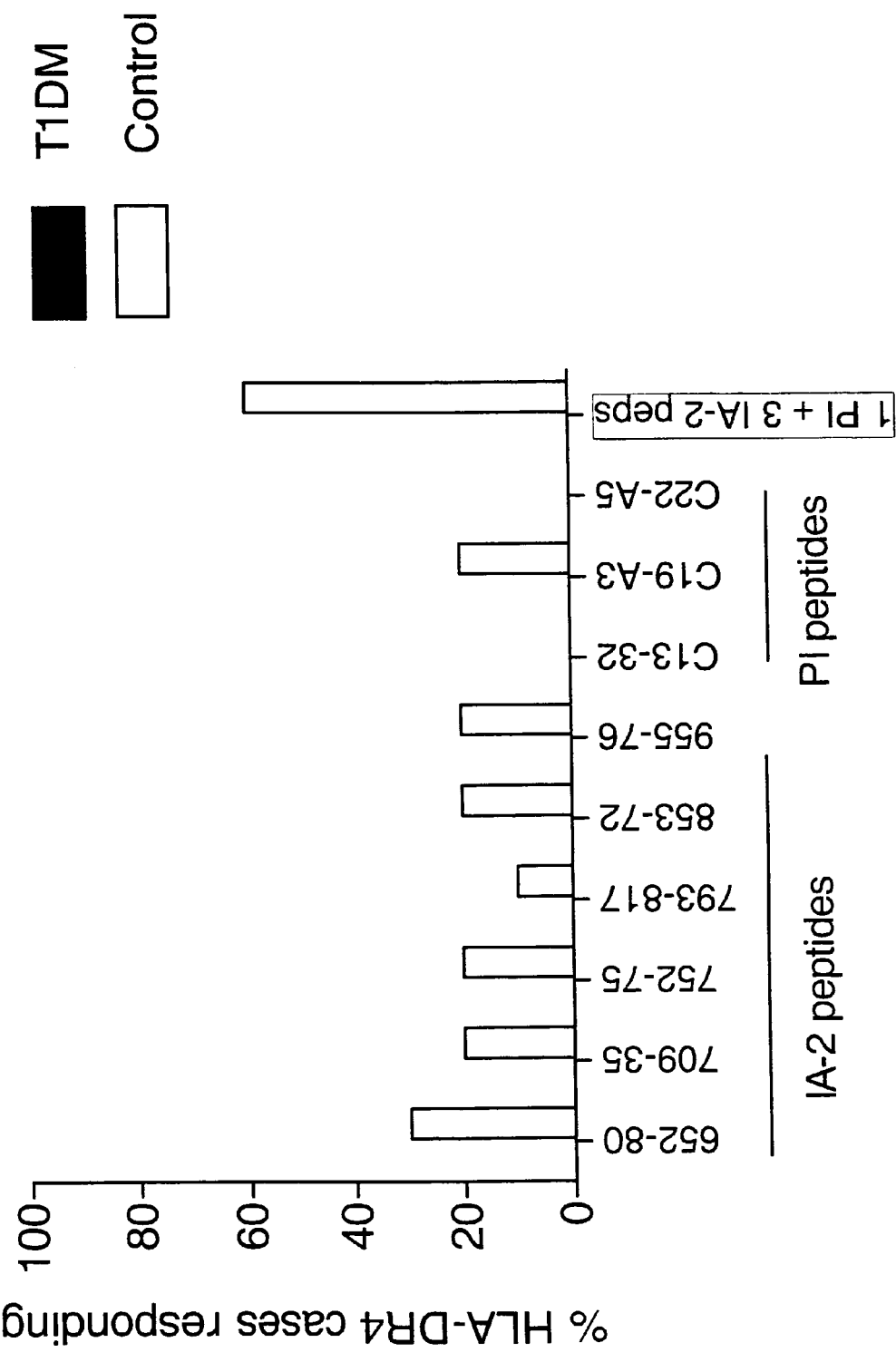
Figure 2. Use of peptides and IL-10 ELISPOT to identify protective CD4 T lymphocytes

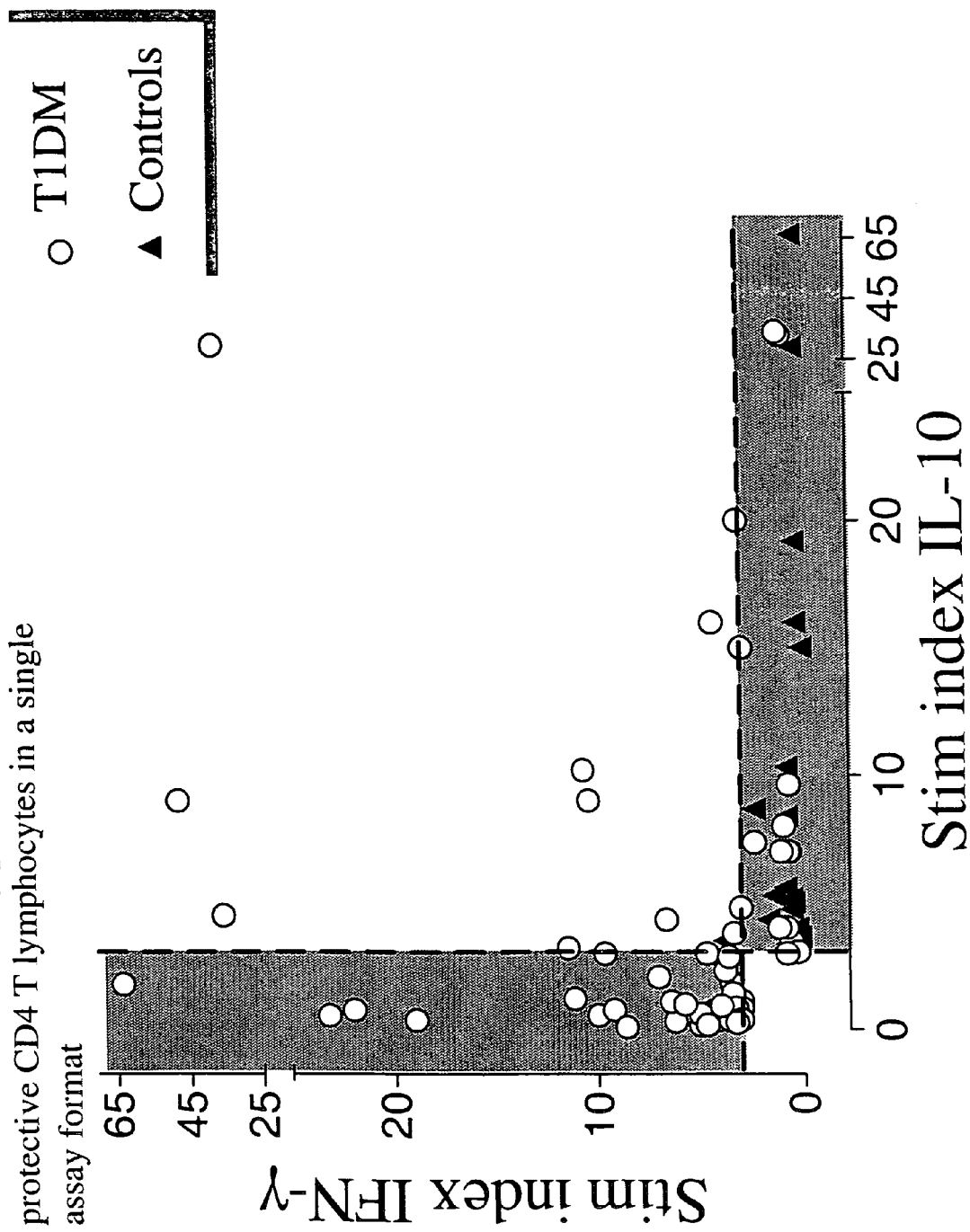
Figure 3. Use of peptides and IFN-γ and IL-10 ELISPOT to identify pathogenic and protective CD4 T lymphocytes in a single assay format

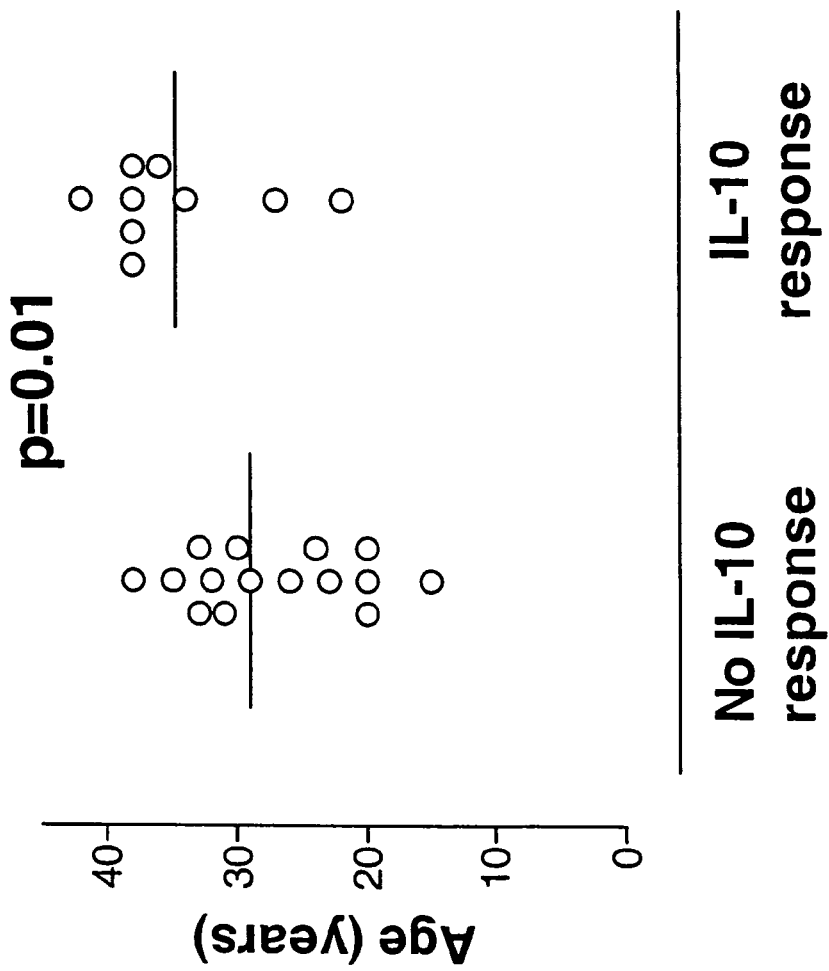
Figure 4. Evidence that anti-inflammatory IL-10 producing CD4+ T lymphocytes that respond to IA-2 and PI peptides delay diabetes onset.

THERAPEUTICALLY EFFECTIVE PEPTIDES RELATED TO PREPROINSULIN

CROSS-REFERENCE TO RELATED APPLICATIONS

This application claims the benefit of Great Britain application GB 402129.1, filed Jan. 30, 2004.

THE FIELD OF THE INVENTION AND ITS OBJECTIVE

This invention relates to autoimmune disease and more particularly to insulin-dependent diabetes mellitus (IDDM or Type 1 diabetes). The objective is the treatment of diabetes using novel peptide combinations and the use of the same peptide combinations in bioassays designed to monitor this, and other diabetes-specific therapies.

In Type 1 diabetes the immune system inadvertently and progressively destroys the cells in the pancreas that make insulin (beta cells). There is thus a loss of immune tolerance to the beta cell. Eventually there are too few beta cells to ensure proper uptake of blood glucose by body cells and the patient has clinical diabetes. The drawbacks of current treatment for this disease are well known, and research effort has been directed over many years to achieving a greater understanding of the disease process with a view to producing improved methods of early diagnosis and more effective therapies. An effective therapy would be one that restores immunological tolerance to the beta cell. This approach would need to be accompanied by a complementary method for the measurement of beta cell tolerance.

It is well understood that the autoimmune attack on beta cells proceeds by way of the MHC class II pathway, in which antigen presenting cells (APCs) process relevant beta cell protein antigens and present their peptide epitopes to CD4+ T lymphocytes, thereby inducing cytokines which assist in the destruction of the beta cells. One approach which has been proposed in the study of Type 1 diabetes and other autoimmune disease has been to isolate (elute) the effective epitopes from the complex of peptide and HLA class II molecule and to explore the potential of these peptides for diagnosis and therapy. U.S. Pat. No. 5,827,516 is directed to this type of approach for a large number of diseases and U.S. Pat. No. 6,562,943 applies this methodology to Type 1 diabetes. Reference may be made to these prior patents to the extent that this may be helpful for a full understanding of the present invention. The literature reference corresponding to U.S. Pat. No. 6,652,943 is Peakman et al, 1999, Naturally processed and presented epitopes of the islet cell autoantigen IA-2 eluted from HLA-DR4, J. Clin Invest 104:1449–1457.

U.S. Pat. No. 6,562,943 mentions three antigens suspected of being involved in Type 1 diabetes, including insulin, pro-insulin, and pre-pro-insulin, but the peptide epitopes disclosed in this patent and eluted from the complex are restricted to those from the postulated IA-2 antigen.

Previous Attempts to Find a Solution

These above mentioned disclosures describe the anticipated utility of these isolated peptides in various ways, for example the following:

(a) As Blocking Peptides

This idea was that a peptide, say for HLA-DR4, would bind very strongly and displace peptides involved in the disease process, thereby preventing activation of autoreactive T cells.

The problem with this idea is that the only way that a natural peptide can block is by competitive exchange so that it occupies all possible HLA binding sites and displaces other occupying peptides. Even the highest binding peptide would struggle to compete to block out all other binders. The peptide would have to compete from outside the cell, where no catalytic enzymes are available to help peptide exchange and where the pH (approximately 7.4 extra—as opposed to 5.0 intra-cellularly) is very unfavourable to peptide exchange. It is estimated that this would require at the very least several milligrams of peptide to get a high enough concentration for effective competition. Since the HLA molecules turn over in a matter of minutes/hours on the cell surface, the competitor peptide would have to be constantly available.

It is highly doubtful whether the system could support this hypothesis and we are aware of no published literature to indicate that such peptides and such a therapeutic application and mode of action have been made and used. Furthermore, such a blocking peptide would be globally immune suppressive, rather than specific for Type 1 diabetes.

(b) Use of Altered Peptides

What was contemplated in this proposal was to alter the natural peptide sequence so that it would still bind to the HLA molecule but, instead of activating the T cell, would send a slightly different signal, which would either switch off the T cell, kill the T cell, or switch the T cell to a more benign type. In the 1990s these altered peptide ligands (APL) with antagonistic properties were considered to be highly promising.

However, when this idea was tried in man it proved very dangerous. The problem was that alteration of the natural peptide could make it immunogenic. In two studies in man (in patients with the autoimmune disease multiple sclerosis) the clinical trials were halted because patients developed dangerous allergic immune responses to the APL. These results were reported in the scientific literature in 2000. A further problem was how to identify what alterations would be successful. This proved to be long painstaking work and there was no indication of which peptide to choose, which amino acid to alter and what to change it to.

Finally, it is noteworthy that to date no bioassay has been described that is capable of measuring tolerance to beta cells.

General Principles of Invention

In accordance, with the present invention we have avoided approaches of the above kind and have focused research effort on ways of suppressing the specific cells involved in the development of this disease. We have concentrated on key epitopes from preproinsulin and have developed a new bioassay to show for the first time that certain of these epitopes are crucially involved in Type 1 diabetes development and may be utilised to achieve natural protection from the disease.

The present invention is directed, first, to the problem of how to specifically inactivate the pathogenic CD4+ T lymphocytes responsible for T1DM. This is achieved by (a) identifying the specific peptides recognised by these cells and (b) using them in a therapeutic modality (termed "peptide immunotherapy"). In peptide immunotherapy (PIT) delivery of soluble native peptide leads to death of the damaging CD4+ T lymphocytes and/or leads to the generation of new ("suppressor") CD4+ T lymphocytes capable of specific suppression of the damaging cells by release of anti-inflammatory cytokines. Such an approach is one of the very few to offer an outcome in which immunological tolerance to beta cells is restored.

A second problem for which a solution is sought is how to monitor the effect of therapies that are designed to inactivate the CD4+ T lymphocytes responsible for T1DM. Such therapies include PIT, but also other approaches, such as immunosuppressive drugs. This monitoring is achieved by (a) identifying the specific peptides recognised by these CD4+ T lymphocytes and (b) using the peptides in an assay that measures the balance of pathogenic and suppressor CD4+ T lymphocytes through the signature cytokines they make. Such a tolerance assay is critical to the general thrust of preventing Type 1 diabetes.

Inactivation of pathogenic CD4+ T lymphocytes that recognise specific peptides in the islets is a difficult challenge. Two approaches have been used in the past. The first and most widely used approach attempts to suppress all CD4+ T lymphocytes. Some of these attempts have been successful in showing that therapies aimed at blocking function of CD4+ T lymphocytes can halt progression of diabetes. This is important proof of concept. However, the major problem is that suppressing all CD4+ T lymphocytes leaves the patient open to a very high risk of infection and tumour development as well as the problem of being on the drug long-term with all of the attendant risks that entails. The benefit-to-risk ratio is thus too low for these drugs to be used.

The second approach to inactivating antigen-specific CD4+ T lymphocytes is by administration of the whole antigen, for example by injection or by nasal spray or orally. There have been attempts with insulin and the published trials have been unsuccessful.

A third way would be to administer specific peptides from the antigen, either as natural peptides or as APLs. Peptides have numerous advantages over the use of whole antigen. Peptides are easy to produce, pharmaceutically formulate and quality assure, they do not carry any of the biological side-effects of the parent molecule and weight for weight provide up to 50 times more of the active component (T cell epitope) than whole antigen. There are no studies on beta cell peptides as therapeutics in Type 1 diabetes in man. In terms of the objective of identifying the beta cell peptide epitopes by elution from HLA, then using bioassays to show which are the peptides that patient CD4+ T lymphocytes respond to and then taking those peptides into a therapy— there have been no other attempts.

We have solved these problems (i.e which peptides to choose for therapy and how to monitor their beneficial effect) in the following ways.

For the problem of choosing which natural peptides to use for therapy, we have extended the approach described in U.S. Pat. No. 6,562,943 to load APCs with antigen, to allow their internalisation, and to identify the peptides that are naturally processed and presented to CD4+ T lymphocytes. In this approach, we have selected preproinsulin as the putative antigen. We have further extended the approach by the inclusion of an additional analytical step, in which natural peptides are screened for recognition by pathogenic CD4+ T lymphocytes, to identify those peptides most important in the disease.

The methodology is described below, including reference to accompanying Tables and Figures.

DESCRIPTION OF FIGURES

FIG. 1. Use of IA-2 and preproinsulin peptides to identify pathogenic (IFN-γ) CD4+ T lymphocytes. Graph shows the percentage of HLA-DR4 cases responding amongst patients (shaded bars) and control non-diabetic subjects (open bars) to each individual IA-2 and preproinsulin (PI) peptides, as well as the response to combinations of peptides from single or multiple antigens. The greatest discrimination between patients and controls using the least peptides occurs when PI C19-A3 is combined with IA-2 709–36, 752–75 and 853–72 to which 76% of patients and 7% of controls respond (p=0.0001). Patient numbers=25, controls=14.

FIG. 2. Use of IA-2 and preproinsulin peptides to identify non-pathogenic, anti-inflammatory (IIL-10 secreting) CD4+ T lymphocytes. Graph shows the percentage of HLA-DR4 cases responding amongst patients (shaded bars) and control non-diabetic subjects (open bars) to each individual IA-2 and preproinsulin (PI) peptides, as well as the response to combinations of peptides from single or multiple antigens by production of IL-10 alone. The greatest discrimination between patients and controls using the least peptides occurs when PI C19-A3 is combined with IA-2 709–36, 752–75 and 853–72 to which 64% of patients and 0% of controls respond (p=0.0001). Patient numbers=25, controls=14.

FIG. 3. Development of an assay that discriminates Type 1 diabetes patients from healthy controls on the basis of their polarization of autoreactive CD4+ T lymphocyte responses to IA-2 and PI peptides. Results of cytokine ELISPOT bioassay is shown for patients with T1DM (open circles) and non-diabetic control subjects (closed triangles). For any given positive peptide response (stimulation index $\geq 3.0$ for IFN-γ or IL-10), the stimulation index for each cytokine has been plotted. There is a highly significant inverse correlation between responses represented by each of these cytokines (p=0.000004), indicating extreme polarization of pro-inflammatory and regulatory autoreactivity. Patients with T1DM are clustered close to the y-axis, and non-diabetic control subjects distributed along the x-axis, indicating the association of disease and tolerant states with pro-inflammatory and regulatory responses, respectively.

FIG. 4. The presence of anti-inflammatory (IL-10) CD4+ T lymphocytes delays the onset of diabetes, indicating that these cells have a protective effect through suppression of pathogenic CD4+ T lymphocytes. This is shown by the relationship between age at onset of T1DM and production of IL-10 in response to peptides of IA-2 and preproinsulin. Of patients tested, those making IL-10 responses are significantly older (p=0.01).

METHODOLOGY 1.1. Identification of Peptides of Preproinsulin Naturally Processed and Presented by HLA-DR4

The procedure we have used for identification of naturally processed and presented peptide epitiopes is a further development of that previously described in U.S. Pat. No. 6,562, 943 and in Peakman et al 1999.

cDNA representing the entire sequence of preproinsulin (embl locus HSPPI, accession X70508.1 obtained from Dr DF Steiner, University of Chicago, Ill.) was cloned into a pET-12a vector (Novagen Inc, Madison Wis.) modified to include a 6-histidine purification tag and biotinylation sequence at the 5' end and transformed into BLR(DE3) pLysS competent cells (Novagen Inc) for expression and purification under denaturing conditions followed by refolding using a glutathione redox reaction and confirmation of correct folding by analysis of V8 protease digestion products. Recombinant preproinsulin was delivered to the surface of APCs (Priess Epstein Barr virus (EBV) transformed B cells, homozygous for the Type 1 DM-permissive DRB1*0401, [DR4/DRw53], DQA1*0301/DQB1*0302 [DQ8] genotype) and HLA-DR4 purified.

Naturally processed peptide repertoires were acid eluted, separated by RP-HPLC, and mass spectra for each 1-minute fraction collected at optimum laser intensities in reflector mode using a time-of-flight mass spectrometer (Voyager Elite; PerSeptive Biosystems, Framingham, Mass.) with both internal and external calibration using synthetic peptides. Synthetic preproinsulin peptides were assessed for their ability to bind soluble HLA-DR4 in vitro in a direct competition binding assay against a biotinylated indicator peptide (98–117 of the MHC class II invariant chain). Binding affinity was expressed as an inhibitory concentration 50 ($IC_{50}$), determined as that required to inhibit binding of 2.5 µM biotinylated indicator peptide by 50%. The preproinsulin peptides that were selected are those with high binding affinity to HLA-DR4 and those that can only be derived from intact preproinsulin. The results are shown in Table 1.

that have been found to exhibit good synergy with preproinsulin C19-A3. These are shown in Table 2.

TABLE 2

IA-2 peptides eluted from HLA-DR4 that have synergy with preproinsulin 75–92

| Numbering in IA-2 | Sequence |
|---|---|
| 709-36 | LAKEWQALCAYQAEPNTCATAQGEGNIK (SEQ ID NO: 11) |
| 752-75 | KLKVESSPSRSDYINASPIIEHDP (SEQ ID NO: 12) |
| 853-72 | SFYLKNVQTQETRTLTQFHF (SEQ ID NO: 13) |

All peptide sequences described herein in accordance with the invention may be modified by the adoption of minor

TABLE 1

Experimentally observed and calculated masses of preproinsulin derived peptides eluted from HLA-DR4, and their matching sequences

| Observed m/z | Calculated m/z | Mass accuracy (ppm) | Residues in preproinsulin | Sequence | $IC_{50}$ for binding to HLA-DR4 (µM) |
|---|---|---|---|---|---|
| 2336.970 | 2337.216 | 85.8 | B27-C15 | TPKTRREAEDLQVGQVELGGGP (SEQ ID NO: 1) | 50 |
| 2305.312 | 2305.203 | 77.9 | C3-C26 | EDLQVGQVELGGGPAGSLQPLAL (SEQ ID NO: 2) | 3 |
| 2305.312 | 2305.203 | 77.9 | C4-C27 | DLQVGQVELGGGPAGSLQPLALE (SEQ ID NO: 3) | 3 |
| 1836.922 | 1836.981 | 32.3 | C13-C32 | GGGPGAGSLQPLALEGSLQK (SEQ ID NO: 4) | 5 |
| 1865.546 | 1866.081 | 286.5 | C19-A3 | GSLQPLALEGSLQKRGIV (SEQ ID NO: 5) | 0.5 |
| 1865.546 | 1866.044 | 267.0 | C22-A5 | QPLALEGSLQKRGIVEQ (SEQ ID NO: 6) | 0.4 |
| 2224.543 | 2225.072 | 250.0 | C25-A12 | ALEGSLQKRGIVEQCCTSICS (SEQ ID NO: 7) | 10 |

Proinsulin sequence:

B-chain: FVNQHLCGSHLVEALYLVCGERGFFYTPKT (SEQ ID NO: 8)  R-R  C-peptide: EAEDLQVGQVELGGGPAGSLQPLALEGSLQ  K-R  A-chain: GIVEQCCTSICSLYQLENYCN Notes:
boxes delineate potential nested sets in which the amino acid in bold represents the most likely P1 residue; in the proinsulin sequence, the dibasic motifs R-R and K-R represent the cleavage sites for removal of C-peptide and these residues are subsequently removed by peptidases The present invention comprises a peptide identified as indicated above and having a sequence comprising or consisting of QPLALEGSLQK (SEQ ID NO: 9). Three peptides containing the above sequence are:

```
GGGPGAGSLQPLALEGSLQK,      (SEQ ID NO: 4)

GSLQPLALEGSLQKRGIV,        (SEQ ID NO: 5)

and

QPLALEGSLQKRGIVEQ          (SEQ ID NO: 6)
``` of which that having the sequence GSLQPLALEGSLQKRGIV (SEQ ID NO: 5) is highly preferred.

Various combinations of these peptides may be used, including a consensus sequence that covers all 3 of these, ie GGGPGAGSLQPLALEGSLQKRGIVEQ (SEQ ID NO: 10).

The location of these sequences in preproinsulin is shown in Table 1.

The present invention also comprises one or more of the above sequences in combination with peptides from IA-2 amino acid differences from the above. For example the peptide may differ from any of the above by up to and including 4 amino acid alterations (substitution and/or deletion and/or insertion) or by extension from any one of the above-mentioned residues at the N-terminus or C-terminus or both with a non-wild-type amino acid sequence.

Our initial screening approach determines which peptides are naturally presented, which have excellent binding characteristics to HLA-DR4, and in the case of preproinsulin, which sequences are unique to this molecule and absent in mature insulin, but not which ones the pathogenic CD4+ T lymphocytes react against during the immune response that leads to Type 1 diabetes. To solve this problem, we have taken the candidate peptides from preproinsulin and others identified from IA-2 in previous work and used them in an assay format called a cytokine ELISPOT. This detects the signature of a CD4+ T cell according to the cytokine it makes. Making interferon-γ (IFN-γ) represents a pathogenic CD4+ T lymphocyte response. The important peptides from a disease point of view are those that elicit a pathogenic response in this assay. This is therefore a very critical refinement of the simple approach to epitope identification above because it reveals which epitopes are important in the disease context.

1.2 Method Used to Identify Pathogenic CD4+ T Lymphocytes: IFN-γ ELISPOT Analysis to Identify Pathogenic Cells Fresh heparinised blood was obtained from 25 Caucasian Type 1 DM patients with HLA-DR4 and acute onset of symptoms, requiring insulin from diagnosis, and from 14 non-diabetic healthy control subjects matched for age and HLA type. Peripheral blood mononuclear cells (PBMCs) were isolated fresh on density gradients (Lymphoprep, Nycom Pharma, Norway) and washed in RPMI 1640 (Life Technologies, Paisley, UK) twice before use. Fresh PBMCs in RPMI 1640 supplemented with antibiotics (TC medium; all Life Technologies) and 10% human AB serum (Harlan SeraLab, Leicestershire, UK) were dispensed into 48-well plates at a density of $2\times10^6$ in 0.5 ml supplemented with peptide to a final concentration of 10 μM and incubated at 37° C., 5% $CO_2$, tilted by 5°. Control wells comprised TC medium containing an equivalent concentration of peptide diluent alone (DMSO), tetanus toxoid (final concentration 100 ng/ml), or PMA/ionomycin (5 ng/ml and 745 ng/ml final concentrations, respectively). On day +1, 0.5 ml pre-warmed TC medium/10%AB was added and on day +2, non-adherent cells were re-suspended using pre-warmed TC medium/ 2% AB, washed, brought to a concentration of $1\times10^6/300$ μl and 100 μl dispensed in triplicate into wells of 96-well ELISA plates (Nunc Maxisorp, Merck, Poole, UK) pre-blocked with 1% BSA in PBS and pre-coated with monoclonal anti-IFN-γ capture antibody (U-Cytech, Utrecht, NL). After capture at 37° C., 5% $CO_2$ for 7 hours, cells were lysed in ice cold water, plates washed in PBS/Tween 20 and spots developed using anti-IFN-γ detection antibody and an appropriate revealing agent. Plates were dried and spots of 80–120 μm counted in a BioReader 3000 (BioSys, Karben, Germany). Mean values in test wells were compared with means of the background (DMSO) wells to derive a stimulation index (SI).

The results are summarised in FIG. 1 and Table 3. FIG. 1 shows the percentage of diabetic patients and controls responding by production of IFN-γ to one or other of the 6 IA-2 peptides and 3 preproinsulin peptides. It is clear that responses are more prevalent in patients and that the greatest discriminative power (between patients and controls) is seen when a minimum of 1 preproinsulin peptide (C19-A3) and 3 IA-2 peptides (709–735, 752–775 and 853–872) are used. In combination, these particular peptides thus represent a cocktail that has the highest achievable disease relevance.

Amongst the 25 patients tested against both IA-2 and PI peptide panels, an IFN-γ response to at least one peptide was seen in 18/25 (72%) T1DM patients, compared with 1/14 (7%) non-diabetic control subjects (p=0.0001). This increase in diagnostic sensitivity was not achieved at the loss of specificity, since none of the non-diabetic control subjects made IFN-γ responses to any of the PI peptides.

Overall, responses to the IA-2 and PI peptides, which had been identified by elution from HLA-DR4, tended to be higher in patients with at least one HLA-DR4-encoding allele. Thus, 15/25 (60%) and 10/17 (59%) patients with at least one HLA-DR4 molecule responded to at least one IA-2 or PI peptide respectively, compared with 4/11 (36%) and 4/8 (50%) of patients with non-DR4 alleles, Similarly, the prevalence of responses to either peptide panel was greater amongst those patients with at least one HLA-DR4 allele (13/17, 76%) compared with those with no-DR4 alleles (5/8, 63%) although none of these trends were significant with the numbers of cases tested in this study.

Additional studies were carried out using samples from 4 T1DM subjects with islet peptide reactive T cells to examine the nature of the responding cells. Positive responses (SI≧3.0) were entirely abolished when PBMCs were depleted of CD4 T cells, indicating that the autoreactive T cells detected are CD4+. In addition, we were able to examine the persistence of IFN-γ T cell responses in a further 4 T1DM patients (all DRB1*0401) from whom a second blood sample was available 15–23 weeks after the first. In three patients there was a positive IFN-γ T cell response (SI≧3.0) in the first sample to at least one IA-2 peptide. In two of these patients, the positive responses remained, whilst in the third, the response to one peptide persisted and to the other declined. The fourth patient showed no response in either sample. These results indicate that, when present, pro-inflammatory autoreactive T cell responses have a tendency to persist during the first months after diagnosis.

TABLE 3

Prevalence of IFN-γ responses to IA-2 and P1 peptides in T1DM patients and non-diabetic control subjects

| | Responses to 1A-2 peptide sequences (SI) | | | | | | Responses to Proinsulin peptide sequences (SI) | | |
|---|---|---|---|---|---|---|---|---|---|
| | 652–80 | 709–35 | 752–75 | 793–817 | 853–72 | 955–76 | C13–32 | C19–A3 | C22–A5 |
| T1DM patients with HLA-DR4 alleles | | | | | | | | | |
| #1 | | | | | 10.0 | | | | |
| #2 | 3.1 | | | | | | | | |
| #3 | 3.0 | | 4.3 | 9.7 | 10 | 4.7 | | 10.7 | |
| #4 | | | | 3.5 | | 3.0 | | 3.5 | |
| #5 | 6.2 | | | | | | | 3.8 | 3.7 |
| #6 | 23.2 | 9.2 | | | 6.6 | 11.2 | 8.6 | 63.6 | 22.0 |
| #7 | | 6.4 | | | | | | | |

TABLE 3-continued

Prevalence of IFN-γ responses to IA-2 and P1 peptides in T1DM patients and non-diabetic control subjects

| | Responses to 1A-2 peptide sequences (SI) | | | | | | Responses to Proinsulin peptide sequences (SI) | | |
|---|---|---|---|---|---|---|---|---|---|
| | 652–80 | 709–35 | 752–75 | 793–817 | 853–72 | 955–76 | C13–32 | C19–A3 | C22–A5 |
| #8 | | | | | | | | 3.0 | |
| #9 | | | | | 5.2 | | | 4.6 | |
| #10 | | | 12.3 | | | | | 5.0 | |
| #11 | | | | | | | | 3.3 | |
| #12 | | | 3.3 | | | | | 10.7 | |
| #13 | | | 3.4 | 4.1 | 3.6 | | | | 3.3 |
| #14 | | | | | | | | | |
| #15 | | | | | | | | | |
| #16 | | | | | | | | | |
| #17 | | | | | | | | | |
| #18 | | | | | | | — | — | — |
| #19 | | 5.0 | 7.0 | 19.0 | | 3.0 | — | — | — |
| #20 | | | 3.9 | | | | — | — | — |
| #21 | | | | | | | — | — | — |
| #22 | | | | | | | — | — | — |
| #23 | | | 3.6 | | | | | | |
| #24 | 36.0 | 10.5 | | | 48.3 | 38.0 | — | — | — |
| #25 | | | | | | | — | — | — |
| Totals (%) | 6/25 (24) | 3/25 (12) | 8/25 (32) | 3/25 (12) | 7/25 (28) | 4/25 (16) | 2/17 (12) | 8/17 (47) | 3/17 (18) |
| T1DM patients with non-DR4 alleles | | | | | | | | | |
| #26 | | | 3.0 | | 5.0 | | | 3.3 | |
| #27 | 16.7 | | | | 3.1 | | | | |
| #28 | | | | | | | 11.5 | 5.0 | 5.8 |
| #29 | | | | | | | 4.7 | | 4.0 |
| #30 | | | | | | 4.7 | | 5.7 | |
| #31 | | | | | | | | | |
| #32 | | | | | | | | | |
| #33 | | | | | | | | | |
| #34 | | | | | 3.7 | | — | — | — |
| #35 | | | | | | | — | — | — |
| #36 | | | | | | | — | — | — |
| Totals (%) | 1/11 (9) | 0/11 (0) | 1/11 (9) | 0/11 (0) | 2/11 (18) | 2/11 (18) | 2/8 (25) | 3/8 (38) | 2/8 (25) |

Non-diabetic control subjects

C1
C2
C3
C4
C5
C6
C7
C8

TABLE 3-continued

Prevalence of IFN-γ responses to IA-2 and P1 peptides in T1DM patients and non-diabetic control subjects

| | Responses to 1A-2 peptide sequences (SI) | | | | | | Responses to Proinsulin peptide sequences (SI) | | |
|---|---|---|---|---|---|---|---|---|---|
| | 652–80 | 709–35 | 752–75 | 793–817 | 853–72 | 955–76 | C13–32 | C19–A3 | C22–A5 |
| C9 | 3.8 | | | | 4.7 | | | | |
| C10 | | | | | | | | | |
| C11 | | | | | | | | | |
| C12 | | | | | | | | | |
| C13 | | | | | | | | | |
| C14 | | | | | | | | | |
| Totals (%) | 1/14 (7) | 0/14 (0) | 0/14 (0) | 0/14 (0) | 1/14 (7) | 0/14 (0) | 0/14 (0) | 0/14 (0) | 0/14 (0) |

– = not done. SI: stimulation index: see methods for details.
Numbers in shaded boxes indicate SI.

2. Tolerance Assay: Development of an Assay to Measure Immunological Tolerance to Beta Cells.

Many/most of the at-risk individuals who may be treated to prevent future diabetes have no symptoms. They are identified as being at risk by a blood test for autoantibodies and genes, either as part of a population-wide screening programme, or because they have a close relative with diabetes. If they have no symptoms or signs, one cannot know whether the therapy is having an effect, without having to wait 5–10 years to see whether they get diabetes or not. In other words, the whole field of intervention therapy in diabetes needs surrogate markers of therapeutic efficacy ("tolerance assays"). Having identified appropriate peptides for use as described above, we have now developed a bioassay that measures tolerance; the balance of pathogenic and suppressor CD4+ T lymphocytes. No such assay has been available hitherto.

For the problem of monitoring immunological tolerance to beta cells, we have extended the approach described in U.S. Pat. No. 6,562,943 to load APCs with antigen, to allow their internalisation, and to identify the peptides that are naturally processed and presented to CD4+ T lymphocytes. In this approach, we have selected preproinsulin as the putative antigen. The methodology is described above (Tables 1–3, FIG. 1). We have used the peptides identified to develop a beta cell tolerance assay.

The following procedures are used.

Fresh heparinised blood was obtained from 25 Caucasian Type 1 DM patients with HLA-DR4 and acute onset of symptoms, requiring insulin from diagnosis, and from 14 non-diabetic healthy control subjects matched for age and HLA type. Peripheral blood mononuclear cells (PBMCs) were isolated fresh on density gradients (Lymphoprep, Nycom Pharma, Norway) and washed in RPMI 1640 (Life Technologies, Paisley, UK) twice before use. Fresh PBMCs in RPMI 1640 supplemented with antibiotics (TC medium; all Life Technologies) and 10% human AB serum (Harlan SeraLab, Leicestershire, UK) were dispensed into 48-well plates at a density of $2 \times 10^6$ in 0.5 ml supplemented with peptide to a final concentration of 10 μM and incubated at 37° C., 5% $CO_2$, tilted by 5°. Positive control wells comprised TC medium containing an equivalent concentration of peptide diluent alone (DMSO), tetanus toxoid (final concentration 100 g/ml), or PMA/ionomycin (5 ng/ml and 745 ng/ml final concentrations, respectively). Negative control wells comprised TC medium containing DMSO alone, or supplemented with equivalent concentrations of the following control peptides; the promiscuous HLA-DR binding MHC class II invariant chain peptide, residues 98–117 PKPPKPVSKMRMATPLLMQA (SEQ ID NO: 14); and three non-autoantigenic peptides from the coxsackievirus B4 P2C protein 55–75 LLESQIATIEQSAPSQSDQEQ (SEQ ID NO: 15), 133–154 AGKSVATNLIGRSLAEK-LNSSV (SEQ ID NO: 16) and 191–213 CQMVSSVD-FVPPMAALEEKGILF (SEQ ID NO: 17) identified as having good binding properties for HLA-DR4 ($IC_{50}$ values 8.2, 2.1 and 0.3 μM respectively).

On day +1, 0.5ml pre-warmed TC medium/10% AB was added and on day +2, non-adherent cells were re-suspended using pre-warmed TC medium/2% AB, washed, brought to a concentration of $1 \times 10^6/300$ μl and 100 μl dispensed in triplicate into wells of 96-well ELISA plates (Nunc Maxisorp, Merck, Poole, UK) pre-blocked with 1% BSA in PBS and pre-coated with either monoclonal anti-IFN-γ or monoclonal anti-IL-10 capture antibody (U-Cytech, Utrecht, NL). After capture at 37° C., 5% $CO_2$ for 7 hours, cells were lysed in ice cold water, plates washed in PBS/Tween 20 and spots developed using either anti-IFN-γ or anti-IL-10 detection antibody and an appropriate revealing agent. Plates were dried and spots of 80–120 μm counted in a BioReader 3000 (BioSys, Karben, Germany). Mean values in test wells were compared with means of the background (DMSO) wells to derive a stimulation index (SI).

Results are shown in Table 4 and FIGS. 2 and 3. FIG. 2 shows the percentage of diabetic patients and controls responding by production of IL-10 alone to one or other of the 6 IA-2 peptides and 3 preproinsulin peptides. It is clear that responses are more prevalent in non-diabetic patients and that the greatest discriminative power (between patients and controls) is seen when the minimum of 1 preproinsulin peptide (C19-A3) and 3 IA-2 peptides (709–735, 752–775 and 853–872) are used. In combination these peptides thus represent the most relevant to identifying the protective phenotype. FIG. 3 shows that the combination of our peptides and an assay that measures IFN-γ and IL-10 responses can discriminate patients and controls very effectively on the basis of the IFN-γ versus IL-10 response.

A striking finding was that more than half of the non-diabetic control subjects (9/14, 64%) made IL-10 responses to IA-2 peptides, compared with a minority of patients with newly-diagnosed T1DM (7/24, 29%; p<0.05, Table 4). These responses were frequently directed against multiple epitopes and of considerable magnitude. Repeated testing one month later in 4 of the non-diabetic control subjects showed that the IL-10 response was reproducible over time (ie 4/4 subjects showed responses classed as positive, SI≧3.0 to the same peptides as in the original assay). Extending this comparison, we noted that the majority of patients with T1DM making IL-10 responses to IA-2 peptides also made IFN-γ responses to the same or another peptide, whereas non-diabetic control subjects making IL-10 responses did so almost entirely in the absence of IFN-γ production. Only 2 patients with T1DM (#33, #35) out of a total of 24 tested (8%) made an isolated IL-10 response to IA-2 peptides, compared with 8/14 (57%) of non-diabetic control subjects (p=0.0019).

Summarising these data on IL-10 responses, there is a clear trend for an IL-10 response against IA-2 peptides to discriminate patients and control subjects (p<0.05). This trend remains for combined anti-IA-2 and anti-PI responses (p=0.08) when only the HLA-DR4 cases and controls are considered (consistent with DR4-eluted peptides being more discriminatory amongst DR4 subjects). IL-10 responses to PI appear non-discriminatory, although fewer cases were studied.

To examine the nature of the relationship between IL-10 and IFN-γ responses to IA-2 and PI peptides in patients and control subjects further, we plotted the SI for each cytokine when a positive peptide response was observed (SI≧3.0 for IFN-γ or IL-10). These results demonstrated a highly significant inverse correlation between responses represented by each of these cytokines (FIG. 3; p=0.000004), indicating that in the context of an autoreactive T cell response there is extreme polarization of pro-inflammatory versus regulatory autoreactivity. Moreover, whilst patients with T1DM were clustered close to the y-axis, non-diabetic control subjects were distributed along the x-axis, highlighting the association of the disease and tolerant states with pro-inflammatory and potentially anti-inflammatory or regulatory responses, respectively. In contrast, there was no inverse correlation between IFN-γ and IL-10 responses to tetanus toxoid (p=0.64). This tendency to make either polarized Th 1 or regulatory T cell responses to naturally processed and presented IA-2 and PI epitopes provides a clear distinction in the quality of autoreactivity between T1DM patients and non-diabetic subjects (p<0.0001).

We made the intriguing finding that patients with T1DM who made IL-10 responses to either IA-2 or PI tended to be significantly older at diagnosis of disease than those who did not (p=0.01; FIG. 4), suggesting that this quality of response is associated with a later disease onset, indicating a protective effect of IL-10 production.

TABLE 4

Prevalence of IL-10 responses to IA-2 and PI peptides in T1DM patients and non-diabetic control subjects

| | Responses to IA-2 peptide sequences (SI) | | | | | | Responses to preproinsulin peptide sequences (SI) | | |
|---|---|---|---|---|---|---|---|---|---|
| | 652–80 | 709–36 | 725–75 | 793–817 | 853–72 | 955–76 | C13–32 | C19–A3 | C22–A5 |
| T1DM patients with HLA-DR4 alleles | | | | | | | | | |
| #2 | | | | | | | | | |
| #3 | 4.8 | | 16.0 | 3.0 | | 3.0 | 7.0 | 10.21 | 7.36 |
| #4 | | | | | | | | | |
| #5 | | 3.5 | | | | | | | |
| #6 | | | | | 4.3 | | | | |
| #7 | | | | | | | | | |
| #11 | | | | | | | | | |
| #12 | | | 3.79 | | | | | | |
| #13 | | | | | | | | | |
| #15 | | | | | | | | | |
| #18 | | | | | | | | | |
| #19 | | | | | | | | | |
| #20 | | | | | | | — | — | — |
| #21 | | | | | | | — | — | — |
| #23 | | | | | | | — | — | — |
| #24 | 4.5 | 9.0 | 15.0 | | 9.0 | 29.5 | — | — | — |
| #25 | | | | | | | — | — | — |
| Totals | 2/17 | 2/17 | 3/17 | 1/17 | 2/17 | 2/17 | 1/12 | 1/12 | 1/12 |
| (%) | (12) | (12) | (18) | (6) | (18) | (6) | (8) | (8) | (8) |
| T1DM patients with non—DR4 alleles | | | | | | | | | |
| #26 | | | | | | | | | |
| #27 | | 7.0 | 33.0 | 34.0 | 20.0 | 4.0 | | 7.0 | 3.0 |
| #28 | | | | | | | | 3.2 | |
| #29 | | | | | | | | | |
| #33 | | | | | | | | | 3.1 |

TABLE 4-continued

Prevalence of IL-10 responses to IA-2 and PI peptides in T1DM patients and non-diabetic control subjects

| | Responses to IA-2 peptide sequences (SI) | | | | | | Responses to preproinsulin peptide sequences (SI) | | |
|---|---|---|---|---|---|---|---|---|---|
| | 652–80 | 709–36 | 725–75 | 793–817 | 853–72 | 955–76 | C13–32 | C19–A3 | C22–A5 |
| #35 | 8.0 | | 4.0 | | 9.6 | | — | — | — |
| #36 | | | | | | | — | — | — |
| Totals | 1/7 | 1/7 | 2/7 | 1/7 | 2/7 | 1/7 | 1/5 | 2/5 | 1/5 |
| (%) | (14) | (14) | (29) | (14) | (29) | (14) | (20) | (40) | (20) |
| Non—diabetic control subjects | | | | | | | | | |
| C1 | | | | | | | | | |
| C2 | | | | | | | | | |
| C3 | | | | 8.7 | | | | | |
| C4 | 5.3 | 3.6 | | 3.4 | | 5.6 | — | — | — |
| C5 | | | | | 4.7 | | | 10.3 | — |
| C6 | | 3.2 | | | | | | | |
| C7 | | | | | | | | | |
| C8 | 4.0 | 16.0 | | | 66.0 | 15.0 | | 29.0 | |
| C9 | | 3.5 | | | | | | | |
| C10 | 8.4 | | | | | | | | |
| C11 | | | | | | 5.2 | | | |
| C12 | | | | | | | | | |
| C13 | | 3.8 | | 3.5 | | | 19.2 | 5.0 | 4.3 |
| C14 | | | | | | | | | |
| Totals | 4/14 | 3/14 | 2/14 | 2/14 | 2/14 | 3/14 | 1/13 | 3/13 | 1/13 |
| (%) | (29) | (21) | (14) | (14) | (14) | (21) | (8) | (23) | (8) |

13 = not done. SI: stimulation index: see methods for details: Numbers in shaded boxes indicate SI.

(1) Specific Therapy for Type 1 Diabetes: The Inventive Solution.

The identification of a specific cocktail of peptides that identifies pathogenic CD4+ T lymphocytes in a majority of patients leads us to the inventive solution of a therapy by which CD4+ T lymphocytes involved in T1DM are inactivated, restoring long-term beta cell tolerance. An important inventive step is our demonstration that the combination of 4 epitopes from 2 autoantigens is vastly superior in terms of its coverage of pathogenic CD4+ T lymphocyte responses. Such coverage gives a greater potency to the therapy, and applicability to a wider range of patients, than any monotherapy hitherto proposed. Thus our therapeutic approach is multi-epitope, multi-antigen peptide immunotherapy and uses the peptides we have identified through a combination of elution and bioassay.

An example of the invention is as follows. The selected peptides are synthesized to GMP grade and pooled into cocktails representing the best possible combined efficacies. Peptides are used singly or pooled in vials containing up to about 1 mg of each peptide per single dose e.g from 0.5 to 5 to 50 to 250 or up to 500 μg in sterile saline and the vial contents administered. In this example administration can be by parenteral or oral or topical routes including intradermal, subcutaneous or intravenous injection, or nasally or orally or epicutaneously as simple solutions. Peptides may also be given in conjunction with tolerance-promoting adjuvants or tolerance promoting cells. Tolerance promoting adjuvants include IL-10 and recombinant cholera toxin B-subunit (rCTB), which are co-administered with peptide. Tolerance promoting cells include immature dendritic cells and dendritic cells treated with vitamin D3, (1alpha,25-dihydroxyvitamin D3) or its analogues. In this example, immature dendritic cells are expanded from patient blood in vitro using standard techniques before the commencement of therapy. Peptides are then bound to the dendritic cells in vitro before administration, which may be by any of the parenteral routes mentioned above. In this example, the administration of peptide in any of these forms takes place on 3 occasions at times 0, 1 and 2 months.

In this example, treatment may be continued according to the indication of primary outcome measures. The primary outcome measures are a change in peptide-induced IL-10+ (increase) and IFN-γ+ (decrease) peptide-reactive cells detected by the cytokine ELISPOT assay or similar changes in IL-10+ and IFN-γ+ cells reactive with epitopes of pre-proinsulin, IA-2 that had not been administered (ie so-called bystander effects). Further primary outcome measures will be changes in basal and stimulated C-peptide levels at 3, 6, and 12 months after commencing treatment and changes in insulin dosage and HbA1c versus placebo, each of which represent enhancement of endogenous insulin production. Any such favourable outcome measures will dictate cessation of therapy; conversely, continuation of presence of or reappearance of, for example IFN-γ+ cells recognising the therapeutic peptides, will dictate continuation of therapy.

In this example, subjects for the therapy are individuals identified as being at-risk of diabetes development in the next 5–10 years through the presence of circulating autoantibodies. Autoantibodies used for this identification are those against preproinsulin, IA-2 and GAD65 and also an autoantibody termed islet cell antibody (ICA). All subjects will have at least one high risk HLA molecule, for example HLA-DR4, -DR3, -DQ8, -DQ2. Subjects can also be newly-diagnosed subjects with Type 1 diabetes, within 3 months of diagnosis and at least one circulating autoantibody as specified above.

(2) A Tolerance Assay to Monitor Therapy for Type 1 Diabetes: The Inventive Solution.

Also in accordance with the present invention we describe hereinafter a tolerance assay that is made up of our peptides plus a cytokine ELISPOT bioassay for use in the monitoring of intervention therapies in patients with, or at risk of Type 1 diabetes. Our identification of a specific cocktail of peptides has led to this invention, in that the peptides can be used (a) to reveal the presence of pathogenic CD4+ T lymphocytes in patients and (b) to reveal the presence of non-pathogenic suppressor CD4+ T lymphocytes that have been induced by preventive therapies. An important inventive step is our demonstration that the combination of 4 epitopes from 2 autoantigens is vastly superior in terms of its coverage of pathogenic and suppressive CD4+ T lymphocyte responses. Thus our diagnostic approach is multi-epitope, multi-antigen screening to monitor the balance of pathogenic versus protective immune responses in patients undergoing therapeutic interventions for Type 1 diabetes.

An example of the invention is as follows. Peptides representing the epitopes having the sequences identified hereinbefore are synthesized to LMP grade and used singly or pooled into cocktails representing the best possible combined efficacies. In this example, a particular immune modulating treatment is commenced with the aim of halting or preventing the autoimmune processes that lead to Type 1 diabetes. An example of this intervention is a course of treatment with peptide immunotherapy, or the non-depleting monoclonal anti-CD3 antibody hOKT3 directed against T cells or an immune suppressive drug such as rapamycin. These therapies are administered for a defined period and then surrogate markers are measured in a tolerance assay to assess the effect of the therapy on pathogenic autoimmunity. An example of a surrogate marker to be used in this way is the cytokine ELISPOT detecting pathogenic (IFN-γ) and suppressor (IL-10) CD4+ T lymphocyte responses to single or cocktails of peptides identified as described above. Reduction or disappearance of pathogenic CD4+ T lymphocytes, or induction of suppressor CD4+ T lymphocytes would lead to a reduction or cessation of therapy. No change or a worsening of these surrogate markers would lead to continuation of therapy and/or the introduction of new reagents. The invention therefore also comprises a method of measuring the state of immunological tolerance of a patient to beta cells which comprises the following steps:

(a) Extracting the patient's peripheral blood mononuclear cells (b) Culturing these cells with any of the peptides or peptide combinations defined hereinbefore (c) Applying a cytokine ELISPOT analysis to the cultured cells in order to quantitate the cellular production of cytokines eg interferon-γ and interleukin-10. The patients immunological tolerance to beta cells is demonstrated by the presence of an increased number of interleukin-10 producing cells and a reduced number of interferon-γ producing cells.

---

SEQUENCE LISTING

```
<160> NUMBER OF SEQ ID NOS: 17

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Pro Lys Thr Arg Arg Glu Ala Glu Asp Leu Gln Val Gly Gln Val
 1               5                  10                  15

Glu Leu Gly Gly Gly Pro
            20

<210> SEQ ID NO 2
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Asp Leu Gln Val Gly Gln Val Glu Leu Gly Gly Gly Pro Gly Ala
 1               5                  10                  15
```

```
Gly Ser Leu Gln Pro Leu Ala Leu
            20

<210> SEQ ID NO 3
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Leu Gln Val Gly Gln Val Glu Leu Gly Gly Pro Gly Ala Gly
 1               5                  10                  15

Ser Leu Gln Pro Leu Ala Leu Glu
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Pro Gly Ala Gly Ser Leu Gln Pro Leu Ala Leu Glu Gly
 1               5                  10                  15

Ser Leu Gln Lys
            20

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Ser Leu Gln Pro Leu Ala Leu Glu Gly Ser Leu Gln Lys Arg Gly
 1               5                  10                  15

Ile Val

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Pro Leu Ala Leu Glu Gly Ser Leu Gln Lys Arg Gly Ile Val Glu
 1               5                  10                  15

Gln

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 7

Ala Leu Glu Gly Ser Leu Gln Lys Arg Gly Ile Val Glu Gln Cys Cys
 1               5                  10                  15

Thr Ser Ile Cys Ser
            20

<210> SEQ ID NO 8
<211> LENGTH: 86
<212> TYPE: PRT
<213> ORGANISM: Artificial Sequence
<220> FEATURE:
<223> OTHER INFORMATION: Description of Artificial Sequence: Synthetic
      proinsulin peptide

<400> SEQUENCE: 8

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Pro Leu Ala Leu Glu Gly Ser Leu Gln Lys
 1               5                  10

<210> SEQ ID NO 10
<211> LENGTH: 26
<212> TYPE: PRT
<213> ORGANISM: Artificial Sequence
<220> FEATURE:
<223> OTHER INFORMATION: Description of Artificial Sequence: Consensus
      peptide

<400> SEQUENCE: 10

Gly Gly Gly Pro Gly Ala Gly Ser Leu Gln Pro Leu Ala Leu Glu Gly
 1               5                  10                  15

Ser Leu Gln Lys Arg Gly Ile Val Glu Gln
            20                  25

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

Leu Ala Lys Glu Trp Gln Ala Leu Cys Ala Tyr Gln Ala Glu Pro Asn
 1               5                  10                  15

Thr Cys Ala Thr Ala Gln Gly Glu Gly Asn Ile Lys
                20                  25

<210> SEQ ID NO 12
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Leu Lys Val Glu Ser Ser Pro Ser Arg Ser Asp Tyr Ile Asn Ala
 1               5                  10                  15

Ser Pro Ile Ile Glu His Asp Pro
                20

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Phe Tyr Leu Lys Asn Val Gln Thr Gln Glu Thr Arg Thr Leu Thr
 1               5                  10                  15

Gln Phe His Phe
            20

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Pro Lys Pro Pro Lys Pro Val Ser Lys Met Arg Met Ala Thr Pro Leu
 1               5                  10                  15

Leu Met Gln Ala
            20

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Leu Glu Ser Gln Ile Ala Thr Ile Glu Gln Ser Ala Pro Ser Gln
 1               5                  10                  15

Ser Asp Gln Glu Gln
            20

<210> SEQ ID NO 16
<211> LENGTH: 22
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 16

Ala Gly Lys Ser Val Ala Thr Asn Leu Ile Gly Arg Ser Leu Ala Glu
 1               5                  10                  15

Lys Leu Asn Ser Ser Val
             20

<210> SEQ ID NO 17
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Gln Met Val Ser Ser Val Asp Phe Val Pro Pro Met Ala Ala Leu
 1               5                  10                  15

Glu Glu Lys Gly Ile Leu Phe
             20
```

The invention claimed is:

1. A method of treating a patient having Type 1 diabetes mellitus (T1DM) or at risk of developing T1DM, which comprises administering to the patient one or more peptides selected from the group consisting of QPLALEGSLQK (SEQ ID NO: 9) and peptides extended therefrom by one or more aminoacids bordering SEQ ID NO:9 in the peptide GGGPGAGSLQPLALEGSLQKRGIVEQ (SEQ ID NO: 10).

2. A method according to claim 1, which comprises administering one or more peptides selected from the group consisting of

```
GGGPGAGSLQPLALEGSLQK,           (SEQ ID NO: 4)

GSLQPLALEGSLQKRGIV,             (SEQ ID NO: 5)

QPLALEGSLQKRGIVEQ,              (SEQ ID NO: 6)

and

GGGPGAGSLQPLALEGSLQKRGIVEQ.     (SEQ ID NO: 10)
```

3. A method according to claim 1, in which the peptide GGGPGAGSLQPLALEGSLQK (SEQ ID NO: 4) is administered.

4. A method according to claim 1, in which the peptide GSLQPLALEGSLQKRGIV (SEQ ID NO: 5) is administered.

5. A method according to claim 1, in which the peptide QPLALEGSLQKRGIVEQ (SEQ ID NO: 6) is administered.

6. A method according to claim 1, in which the peptide GGGPGAGSLQPLALEGSLQKRGIVEQ (SEQ ID NO: 10) is administered.

7. A method according to claim 1 or 2, in which a selected peptide is administered together with one or more peptides selected from the group consisting of

```
LAKEWQALCAYQAEPNTCATAQGEGNIK,   (SEQ ID NO: 11)

KLKVESSPSRSDYINASPIIEHDP,       (SEQ ID NO: 12)

and

SFYLKNVQTQETRTLTQFHF.           (SEQ ID NO: 13)
```

8. A method according to claim 1 or 2, in which a selected peptide is administered together with a peptide or peptides selected from the group consisting of

| | | | |
|---|---|---|---|
| a. | IA-2 752-75 | (SEQ ID NO: 12) |
| b. | IA-2 853-72 | (SEQ ID NO: 13) |
| c. | IA-2 709-36 | (SEQ ID NO: 11) |
| d. | IA-2 752-75 | (SEQ ID NO: 12) |
| | and | |
| | IA-2 853-72 | (SEQ ID NO: 13) |
| e. | IA-2 709-36 | (SEQ ID NO: 11) |
| | and | |
| | IA-2 752-75 | (SEQ ID NO: 12) |
| f. | IA-2 709-36 | (SEQ ID NO: 11) |
| | and | |
| | IA-2 853-72, | (SEQ ID NO: 13) |
| | and | |
| g. | IA-2 709-36 | (SEQ ID NO: 11) |

-continued

```
        and

IA-2 752-75       (SEQ ID NO: 12)

and

IA-2 853-72.      (SEQ ID NO: 13)
```

9. A method of treatment or prevention of Type 1 diabetes according to claim 1 or 2, the selected peptide or peptides being administered by parenteral or oral or topical routes, including intradermal, subcutaneous or intravenous injection, or nasally or epicutaneously.

10. A method according to claim 9, in which the peptide or each peptide is administered in an amount of up to 1 mg per single dose.

11. A method according to claim 10, in which the peptide or each peptide is administered in an amount of from 0.5 to 500 micrograms per single dose.

12. A method according to claim 11, in which a single dose contains from 5 to 250 µg of the, or each, peptide.

13. An isolated peptide selected from the group consisting of GGGPGAGSLQPLALEGSLQK (SEQ ID NO: 4), GSLQPLALEGSLQKRGIV (SEQ ID NO: 5), QPLALEGSLQKRGIVEQ SEQ ID NO: 6) and GGGPGAGSLQPLALEGSLQKRGIVEQ (SEQ ID NO: 10).

14. The isolated peptide

```
GGGPGAGSLQPLALEGSLQK.    (SEQ ID NO: 4)
```

15. The isolated peptide

```
GSLQPLALEGSLQKRGIV.      (SEQ ID NO: 5)
```

16. The isolated peptide

```
QPLALEGSLQKRGIVEQ.       (SEQ ID NO: 6)
```

17. The isolated peptide

```
GGGPGAGSLQPLALEGSLQKRGIVEQ.   (SEQ ID NO: 10)
```

18. A composition comprising a first peptide selected from the group consisting of QPLALEGSLQK (SEQ ID NO: 9), and peptides extended therefrom by one or more aminoacids bordering SEQ ID NO:9 in the peptide GGGPGAGSLQPLALEGSLQKRGIVEQ (SEQ ID NO: 10), said composition also comprising one or more peptides selected from the group consisting of LAKEWQALCAYQAEPNTCATAQGEGNIK (SEQ ID NO: 11),

```
KLKVESSPSRSDYINASPIIEHDP,   (SEQ ID NO: 12)
and

SFYLKNVQTQETRTLTQFHF.       (SEQ ID NO: 13)
```

19. A composition comprising a first peptide according to claim 13, and also comprising a peptide or peptides selected from LAKEWQALCAYQAEPNTCATAQGEGNIK (SEQ ID NO: 11), KLKVESSPSRSDYINASPIIEHDP (SEQ ID NO: 12), and SFYLKNVQTQETRTLTQFHF (SEQ ID NO: 13).

20. A composition according to claim 19, comprising a first peptide according to claim 13 and also comprising a peptide or peptides selected from the group consisting of

```
h.   IA-2 752-75      (SEQ ID NO: 12)

i.   IA-2 853-72      (SEQ ID NO: 13)

j.   IA-2 709-36      (SEQ ID NO: 11)

k.   IA-2 752-75      (SEQ ID NO: 12)

and

IA-2 853-72      (SEQ ID NO: 13)

l.   IA-2 709-36      (SEQ ID NO: 11)

and

IA-2 752-75      (SEQ ID NO: 12)

m.   IA-2 709-36      (SEQ ID NO: 11)

and

IA-2 853-72,     (SEQ ID NO: 13)
and n.   IA-2 709-36      (SEQ ID NO: 11)

and

IA-2 752-75      (SEQ ID NO: 12)

and IA-2 853-72. (SEQ ID NO: 13)
```

21. A pharmaceutical composition comprising a peptide according to claim 13, in which the peptide or each peptide is conjugated or otherwise combined with a tolerance-promoting adjuvant or tolerance promoting cells.

22. A pharmaceutical composition comprising a peptide combination according to claim 18 or 19, in which the peptide or each peptide is conjugated or otherwise combined with a tolerance-promoting adjuvant or tolerance promoting cells.

23. A diagnostic method or kit for diagnosis of, or determination of a predisposition to, Type 1 diabetes, comprising a peptide or composition according to claim 13, 18 or 19.

24. A diagnostic method or kit for diagnosis of, or determination of a predisposition to, Type 1 diabetes, comprising a composition according to claim 20.

25. A method of treating a patient having Type 1 diabetes mellitus (T1DM) or at risk of developing T1DM, which comprises administering to the patient one or more peptides selected from the group consisting of GGGPGAGSLQPLALEGSLQK (SEQ ID NO: 4), GSLQPLALEGSLQKRGIV (SEQ ID NO: 5), QPLALEGSLQKRGIVEQ (SEQ ID NO: 6) and GGGPGAGSLQPLALEGSLQKRGIVEQ (SEQ ID NO: 10).

\* \* \* \* \*